United States Patent [19]

Schwan

[11] 4,002,626
[45] Jan. 11, 1977

[54] 1-(2-NAPHTHYLMETHYL)-3,4,5,6-TETRAHYDRO-2(1H)PYRIMIDONE

[75] Inventor: Thomas J. Schwan, Norwich, N.Y.

[73] Assignee: Morton-Norwich Products, Inc., Norwich, N.Y.

[22] Filed: Mar. 15, 1976

[21] Appl. No.: 666,754

[52] U.S. Cl. .......................... 260/251 R; 424/251
[51] Int. Cl.$^2$ ..................................... C07D 239/04
[58] Field of Search ............................... 260/251 R

[56] References Cited

FOREIGN PATENTS OR APPLICATIONS 877,306  4/1959  United Kingdom ........... 260/251 R Primary Examiner—Lewis Gotts
Assistant Examiner—D. R. Phillips
Attorney, Agent, or Firm—Anthony J. Franze

[57] ABSTRACT

1-(2-Naphthylmethyl)-3,4,5,6-tetrahydro-2(1H)pyrimidone possesses pharmacological activity as an antianxiety agent and as an antidepressant agent.

1 Claim, No Drawings

1-(2-NAPHTHYLMETHYL)-3,4,5,6-TETRAHYDRO-2(1H)PYRIMIDONE

This invention relates to chemical compounds. In particular it is concerned with a compound of the formula:

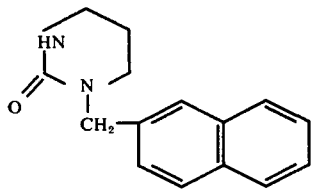

which possesses pharmacological activity affecting the central nervous system. When administered perorally to animals it exhibits antianxiety activity and antidepressant activity. Its antianxiety action is evidenced in the control of pentylenetetrazol induced toxic extensor seizures in mice. An oral dose of 200 mg/kg of this compound to mice intravenously receiving 45 mg/kg of pentylenetetrazol counteracts the effects of pentylenetetrazol.

Its antidepressant property is evidenced in the control of tetrabenazine-induced ptosis in mice. An oral dose of 200 mg/kg of this compound to mice intraperitoneally receiving 35 mg/kg of tetrabenazine counteracts the ptosis producing propensity of tetrabenazine.

In order that this invention be readily available to and understood by those skilled in the art the following illustration is included:

A. 1-(2-Naphthylmethyl)2-(1H)-pyrimidone

A 14.6 g (0.11 mole) portion of 2-hydroxypyrimidine hydrochloride in 700 ml of methanol was treated with 23.3 g (0.22 mole) of $Na_2CO_3$, 7.5 g (0.05 mole) of NaI and 20.0 g (0.11 mole) of 2-(chloromethyl) naphthalene. The reaction mixture was refluxed for 18 hrs and concentrated to dryness under reduced pressure. The solid was taken up in 200 ml of $H_2O$ and extracted with 300 ml of $CHCl_3$. The chloroform extract was washed with 100 ml of $H_2O$, dried over $MgSO_4$ for 2 hrs and filtered. The filtrate was concentrated under reduced pressure to give 24 g (92%) of a cream solid, m.p. 136°–145°.

The product was recrystallized from 110 ml of acetonitrile, washed with acetonitrile, ether and dried to give 15.8 (61%) of a white solid, m.p. 157°–158°.

B. 1-(2-Naphthylmetyl)-3,4,5,6-tetrahydro-2(1H)-pyrimidone

A 15.8 g (0.067 mole) portion of A., 150 ml of methanol and 0.2 g of $PtO_2$ were placed in a 0.5 L pressure bottle and subjected to hydrogenation at 34 psig. The hydrogen uptake was complete in 7 hrs. The reduction mixture was warmed, decolorized and filtered. The filtrate was concentrated under reduced pressure to give 16.0 g (99%) of a white solid, m.p. 151°–155°.

The product was recrystallized from 125 ml of acetonitrile, washed with acetonitrile, ether and dried, m.p. 156°–158°. Yield: 1.5 g (72%).

An analytical sample, m.p. 156°–158°, was recyrstallized from acetonitrile.

Anal. Calcd. for $C_{15}H_{16}N_2O$: C, 74.97; H, 6.71; N, 11.66, Found: C, 74.81; H, 6.81; N, 11.48.

What is claimed is:

1. A compound of the formula:

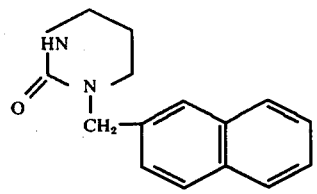

* * * * *